US009458425B1

(12) United States Patent
Itskovitz-Eldor et al.

(10) Patent No.: US 9,458,425 B1
(45) Date of Patent: *Oct. 4, 2016

(54) DIFFERENTIATED HUMAN EMBRYOID CELLS AND A METHOD FOR PRODUCING THEM

(75) Inventors: Joseph Itskovitz-Eldor, Haifa (IL); Nissim Benvenisty, Jerusalem (IL)

(73) Assignees: TECHNION RESEARCH AND DEVELOPMENT FOUNDATION LTD., Haifa (IL); YISSUM RESEARCH DEVELOPMENT COMPANY OF THE HEBREW UNIVERSITY OF JERUSALEM, Jerusalem (IL)

( * ) Notice: Subject to any disclaimer, the term of this patent is extended or adjusted under 35 U.S.C. 154(b) by 1087 days.

This patent is subject to a terminal disclaimer.

(21) Appl. No.: 09/979,001

(22) PCT Filed: May 12, 2000

(86) PCT No.: PCT/IL00/00270
§ 371 (c)(1),
(2), (4) Date: Aug. 5, 2002

(87) PCT Pub. No.: WO00/70021
PCT Pub. Date: Nov. 23, 2000

(30) Foreign Application Priority Data

May 14, 1999 (IL) .......................................... 129966

(51) Int. Cl.
| | |
|---|---|
| C12N 5/0735 | (2010.01) |
| C12N 5/02 | (2006.01) |
| C12N 5/073 | (2010.01) |
| A61K 35/12 | (2015.01) |

(52) U.S. Cl.
CPC ............. *C12N 5/0603* (2013.01); *A61K 35/12* (2013.01); *C12N 5/0606* (2013.01); *C12N 2501/115* (2013.01)

(58) Field of Classification Search
CPC ............. C12N 5/0603; C12N 5/0606; C12N 2501/115; A61K 35/12
USPC ....... 435/325, 363, 366, 374, 377, 404, 405, 435/395, 401
See application file for complete search history.

(56) References Cited

U.S. PATENT DOCUMENTS

| 5,877,299 | A * | 3/1999 | Thomas et al. ............... 530/413 |
| 6,200,806 | B1 * | 3/2001 | Thomson ...................... 435/366 |
| 6,602,711 | B1 * | 8/2003 | Thomson et al. ............. 435/378 |
| 7,045,353 | B2 * | 5/2006 | Benvenisty ................... 435/377 |
| 2003/0175954 | A1 * | 9/2003 | Shamblott et al. ........... 435/366 |

FOREIGN PATENT DOCUMENTS

| AU | 199925106 B2 | 7/1999 |
| AU | 2001286173 B2 | 7/2001 |
| CA | 2 315 538 A1 | 7/1999 |
| DE | 19756864 C1 | 4/1999 |
| JP | 06038742 A | 2/1994 |
| WO | WO 96/16162 | 5/1996 |
| WO | WO 98/43679 | 10/1998 |
| WO | WO 99/32606 | 7/1999 |
| WO | 00/15764 A2 | 3/2000 |
| WO | WO 00/34525 | 6/2000 |

OTHER PUBLICATIONS

Verfaillie et al. Hematology (Am Soc Hematol Educ Program). 2002;:369-91.*
Jones and Thomson. Semin. Reprod. Medicine, 18(2):219-23 (2000).*
Pera. Curr. Opinion. Genet. Dev., 11(5):595-9 (Oct. 2001).*
Shamblott et al. PNAS, 95: 13726-13731 (Nov. 1998).*
Nakashima et al. Hum. Pathol., 19(10):1144-54 (1988).*
Itskovitz-Eldor. Molecular Medicine, 6(2):88-95 Feb. 2000).*
Keller. Curr. Opinion in Cell Biology, 7:862-869 (1995).*
Thomson. Science, 282:1145-1147 (1998).*
Encyclopædia Britannica [online]. [Retrieved on Jan. 17, 2006]. Retrieved from the Internet: URL:http://www.search.eb.com/thesaurus?hdwd=derive&book=Thesaurus&jump=derive+from%5Bverb%5D&list=derive%5Bverb%5D%3D108794%3Bderive+from%5Bverb%5D%3D108810>.*
Dean et al. Development, 125:2273-2282,1998.*
Fujimoto et al. Stem Cells. 24:595-603 (2006).*
Onyango et al. Pnas, 99(16): 10599-10604, Aug. 6, 2002.*
Miki et al. Genesis, 41:81-86, 2005.*
Mikkola et al. BMC Dev. Bio, 6: 1-11, 2006.*
Hanson et al. APMIS, 113:751-5, 2005.*
Maitra et al. Nature Genetics, 37(10): 1099-1103 2005.*
"DNA methylation" and Karyotype from Dictionary.com, accessed online on Jan. 4, 2008.*
Reubinoff et al. Nature Biotech., 18: 399-404, 2000.*
Benvenisty Declaration from U.S. Appl. No. 09/918,702, filed Mar. 21, 2005, pages.*
Amit et al., Developmental Biology, 227: 271-278, 2000.*
Grounds for interlocutory decision in Opposition Proceedings on application EP 94 913 174 (Jul. 21, 2003).
Gerald Bain et al., "Embryonic Stem Cells Express Neuronal Properties In Vitro", *Developmental Biology*, 1995, pp. 342-357, vol. 168.

(Continued)

*Primary Examiner* — Thaian N Ton
(74) *Attorney, Agent, or Firm* — Browdy and Neimark, PLLC

(57) ABSTRACT

A process for obtaining human derived embryoid bodies (hEB). Human embryonic stem cells are incubated in vitro in a liquid growth medium under conditions in which the cells undergo differentiation, but do not adhere to the walls of the container. The invention also provides hEBs obtained by the process.

1 Claim, 4 Drawing Sheets

(56) References Cited

OTHER PUBLICATIONS

Mario R. Capecchi, "Altering the Genome by Homologous Recombination", *Science*, 1989, pp. 1288-1292, vol. 244.

J.M. Chirgwin et al., "Isolation of Biologically Active Ribonucleic Acid from Sources Enriched in Ribonuclease", *Biochemistry*, 1979, pp. 5294-5299, vol. 18.

M. Dushnik-Levinson et al, "Embryogenesis in vitro: Study of Differentiation of Embryonic Stem Cells", *Biology of the Neonate*, 1995, pp. 77-83, vol. 67.

J. Itskovitz-Eldor et al., "Differentiation of Human Embryonic Stem Cells into Embryonic Bodies Comprising the Three Embryonic Germ Layers", *Molecular Medicine*, 2000, pp. 88-95, vol. 6, No. 2.

Julien et al., "Cloning and Developmental Expression of the Murine Neurofilament Gene Family", *Brain Research*, 387:243-50(1986).

Krumlauf et al., "Developmental Regulation of a α-Fetoprotein Genes in Transgenic Mice", *Molecular and Cellular Biology*, 5:1639-48(1985).

Leder et al., "Characterization, Expression and Evolution of the Mouse Embryonic ζGlobin Gene", *Molecular and Cellular Biology*, 5:1025-33(1985).

M. Levinson-Dushnik et al., "Involvement of Hepatocyte Nuclear Factor 3 in Endoderm Differentiation of Embryonic Stem Cells", *Molecular and Cellular Biology*, Jul. 1997, pp. 3817-3822, vol. 17, No. 7.

M.H. Undenbaum et al, "An in vitro Globin gene Switching Model Based on Differentiated Embryonic Stem Cells", *Genes & Development*, 1990, pp. 2075-2085, vol. 4.

C.L. Mummery et al., "Fibroblast-Mediated Growth Regulation and Receptor Expression in Embryonal Carcinoma and Embryonic Stem Cells and Human Germ Cell Tumors", *Biochemical and Biophysical Research Communications*, 1993, pp. 188-195, vol. 191, No. 1.

T. Nakamura et al., "A Selective Switch-On System for Self-Renewal of Embryonic Stem Cells Using Chimeric Cytokine Receptors", *Biochemical and Biophysical Research Communications*, 1998, pp. 22-27, vol. 248, No. 1.

M.F. Pera et al., "Human Embryonic Stem Cells", *Journal of Cell Sciences*, 2000, pp. 5-10, vol. 113.

P.D. Rathjen et al., "Properties and Uses of Embryonic Stem Cells: Prospects for Application to Human Biology and gene Therapy" *Reproduction. Fertility and Development*, 1998, pp. 31-47, vol. 10, No. 1.

E. Robertson, "Embryo-Derived Stem Cell Lines", from *Teratocarcinoma and Embryonic Stem Cells: A Practical Approach*, 1987, pp. 71-112, Oxford.

Rossant et al., "Towards a Molecular Genetic Analysis of mammalian Development", *Trends in Genetics*, 1989, pp. 277-283, vol. 5, No. 8

Sanchez, A., Jones, W.K., Gulick, J., Doetschrnan, T., Robbins, J., "Myosin Heavy Chain Gene Expression in Mouse Embryoid Bodies", *Journal of Biological Chemistry*, 265:22419-26(1991).

Sassoon, D.A., Gamer, I., Buckingham. M., "Transcripts of α-cardiao and α-skeletal actin are early markers for myogenesis in the mouse embryo", *Development*, 104:155-64(1088).

Southern, E.M., "Detection of Specific Sequences Among DNA Fragments Separated by Gel Electrophoresis", *Journal of Molecular Biology*, 98:503-17(1975).

J.A. Thompson et al., "Pluripotent Cell Lines Derived from Common Marmoset (*Callithrix jacchus*) Blastocysts", *Biology of Reproduction*, 1996, pp. 254-259, vol. 55.

J.A. Thompson et al., "Isolation of a Primate Embryonic Stem Cell Line", *Proceedings of the National Academy of Sciences of the United States of America*, Aug. 1995, pp. 7844-7848, vol. 92.

J.A. Thompson et al., "Primate Embryonic Stem Cells", *Current Topics in Developmental Biology*, 1998, pp. 133-165, vol. 38.

M.V. Wiles et al., "Multiple Hematopoietic Lineages Develop from Embryonic Stem (ES) Cells in Culture", *Development*, 1991, pp. 259-267, vol. 111.

A.M. Wobus et al., "Characterization of a Pluripotent Stem Cell Line Derived from a Mouse Embryo", *Experimental Cell Research*, 1984, pp. 212-219, vol. 152.

Reubinoff et al.,"Embryonic stem cell lines from human blastocysts: somatic differentiation in vitro" Nature Biotechnology, 18:399-404 (Apr. 2000).

Kyuwa et al.,"Characterization of Embryonic Stem-Like Cell Lines Derived from Embryoid Bodies" Exp. Anim. 46(1) 11-16 (1997).

Nakashima et al.,"Characteristics of "Embryoid Body" In Human Gonadal Germ Cell Tumors" Hum. Pathol., vol. 19, pp. 1144-1154 (1998).

Thomson et al., "Pluripotent Cell Lines Derived from Marmoset (*Callithrix jacchus*) Blastocysts" Biology of Reproduction, 55:254-259 (1996).

\* cited by examiner

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial
<220> FEATURE:
<223> OTHER INFORMATION: synthetic

<400> SEQUENCE: 1
agaacctgtc acaagctgtg                                              20
```

<210> SEQ ID NO 2
<211> LENGTH: 20
<212> TYPE: DNA
<213> ORGANISM: Artificial
<220> FEATURE:
<223> OTHER INFORMATION: synthetic

<400> SEQUENCE: 2
gacagcaagc tgaggatgtc                                              20

<210> SEQ ID NO 3
<211> LENGTH: 20
<212> TYPE: DNA
<213> ORGANISM: Artificial
<220> FEATURE:
<223> OTHER INFORMATION: synthetic

<400> SEQUENCE: 3
gactgagagg accatcattg                                              20

<210> SEQ ID NO 4
<211> LENGTH: 20
<212> TYPE: DNA
<213> ORGANISM: Artificial
<220> FEATURE:
<223> OTHER INFORMATION: synthetic

<400> SEQUENCE: 4
tcaggacaga ggatacgacc                                              20

<210> SEQ ID NO 5
<211> LENGTH: 21
<212> TYPE: DNA
<213> ORGANISM: Artificial
<220> FEATURE:
<223> OTHER INFORMATION: synthetic

<400> SEQUENCE: 5
agccacatcg ctcagacacc a                                            21

<210> SEQ ID NO 6
<211> LENGTH: 20
<212> TYPE: DNA
<213> ORGANISM: Artificial
<220> FEATURE:
<223> OTHER INFORMATION: synthetic

<400> SEQUENCE: 6
gtactcagcg gccagcatcg                                              20

<210> SEQ ID NO 7
<211> LENGTH: 50
<212> TYPE: DNA
<213> ORGANISM: Artificial
<220> FEATURE:
<223> OTHER INFORMATION: synthetic

<400> SEQUENCE: 7
ttgtccctct tcagcaaagc agacttcctg ttcctggcct tggcagcatt             50

<210> SEQ ID NO 8
<211> LENGTH: 50
<212> TYPE: DNA
<213> ORGANISM: Artificial
<220> FEATURE:
<223> OTHER INFORMATION: synthetic

```
<400> SEQUENCE: 8
tgatggtcct ctcagtcttg gtcagagaca tggcggcagg gtgggcagct                50

<210> SEQ ID NO 9
<211> LENGTH: 50
<212> TYPE: DNA
<213> ORGANISM: Artificial
<220> FEATURE:
<223> OTHER INFORMATION: synthetic

<400> SEQUENCE: 9
cctgcgtgcg gatggacttg aggtcgttgc tgatggcggc tacctggctc                50

<210> SEQ ID NO 10
<211> LENGTH: 50
<212> TYPE: DNA
<213> ORGANISM: Artificial
<220> FEATURE:
<223> OTHER INFORMATION: synthetic

<400> SEQUENCE: 10
cggtggacaa tggatgggcc tgcctcatcg tactcttgct tgctaatcca                50
```

DIFFERENTIATED HUMAN EMBRYOID CELLS AND A METHOD FOR PRODUCING THEM

REFERENCE TO RELATED APPLICATIONS

The present application is the national stage under 35 U.S.C. 371 of international application PCT/IL00/00270, filed May 12, 2000, which designated the United States, and which international application was published under PCT Article 21(2) in the English language.

FIELD OF THE INVENTION

The present invention is in the field of cell biology and more specifically relates to methods of in vitro differentiation.

BACKGROUND OF THE INVENTION

Embryonic stem (ES) cells are derived from totipotent cells in an embryo. Murine ES cells have been shown to be pluripotent cells capable in vitro of terminal differentiation into cells of the mesoderm, ectoderm and endoderm lineages (Robertson, 1987; Dushnik-Levinson and Benvenisty, 1995). The pluripotency of murine embryonic stem cells has been established on the basis of three criteria:
  (1) When undifferentiated murine ES cells are injected into the cavity of a blastocyst and the blastocysts are subsequently implanted into pseudo-pregnant mice, chimeric mice develop. The injected ES cells contribute to all cell types, including the germ layer. Thus, in the next generation, mice with the genotype of the ES cells are born (Capecchi, 1989; Rossant and Joyner, 1989).
  (2) When murine ES cells are injected subcutaneously into syngeneic mice, teratoma tumors develop. These tumors comprise cells of all three embryonic origins (endoderm, ectoderm and mesoderm) (Wobus et al., 1984).
  (3) When murine ES cells are allowed to aggregate in vitro so as to form embryoid bodies (EBs), the cells differentiate in the EBs into various cell types (Robertson, 1987).

During maturation of murine ES cells in vitro, in addition to morphological changes, a cell may acquire a molecular marker characteristic of a differentiated cell type, such as ζ-globin (a marker of hematopoietic cells) (Wiles and Keller, 1991; Lindenbaum and Grosveld, 1990), neurofilament-68 kd protein (a marker of neuronal cells) (Bain et al., 1995; Levinson-Dushnik and Benvenisty, 1997), and albumin (a marker of hepatic cells) (Levinson-Dushnik and Benvenisty, 1997).

ES cell lines have also been established from primates such as the common marmoset (Thomson. 1996), and the rhesus monkey (Thomson, 1995). However, EB formation by marmoset ES cells is inconsistent and asynchronous, and differentiation of the rhesus ES cells is disorganized and vesicular structures do not form (Thomson, 1998a).

Human ES cell lines have been established derived from human embryos produced by in vitro fertilization (Thomson, 1998b). The embryos were cultured to the blastocyst stage and inner cell masses comprising ES cells were isolated and cultured. These human ES cells are only known to be capable of differentiating when in teratomas (Thomson, 1998b). When cultured in vitro, the human ES cells have normal karotypes, express telomerase activity, and proliferate. However, the inability to produce EBs from non-human primate ES cells led to the belief that EBs could also not be formed from human ES cells (Thomson, 1998a).

SUMMARY OF THE INVENTION

The present invention is based on the finding that, contrary to the aforementioned belief that human ES cells do not form EBs, under appropriate conditions, human embryoid bodies (hEBs) may be obtained in vitro from human ES (hES) cells suspended in a liquid medium. These hEBs contain mesoderm, ectoderm and endoderm cell lineages and may be used as a source of cells of the different lineages, e.g., for transplantation or inoculation into human recipients. By incubating the hEBs, these basic cell lineages can differentiate into a wide variety of different cell types, e.g., cells having characteristics of cardiac cells, neural stem cells, and others.

The hEBs in accordance with the invention may be used as a source of cells for use in transplantation or inoculation into a human recipient in order to treat various diseases or disorders, to assist in tissue repair, or to substitute for degenerated tissue.

Thus, in accordance with one aspect, the present invention provides a human embryoid body (hEB).

The hEB, in accordance with the invention, is preferably obtained by in vitro culturing of hES cells in a vessel under conditions in which the cells or aggregates thereof do not adhere to the vessel walls.

In accordance with another aspect, the invention provides a process for obtaining at least one human-derived embryoid body (hEB), comprising:
  (a) providing human embryonic stem (hES) cells;
  (b) growing the hES cells in vitro in a vessel under conditions in which said cells undergo differentiation and the cells or aggregates thereof do not adhere to the vessel wall;
  and
  (c) incubating for a time sufficient to develop hEBs from said cells.

The conditions whereby the hES cells do not adhere to the vessel wall include culturing the cells in a vessel having walls made of a material to which the cells or aggregates thereof are incapable of adhering, adding one or more factors into the medium which prevent adherence of the cells to the vessel walls, etc. Conditions whereby the hES undergo differentiation include the absence of inhibitors of differentiation, such as leukemia inhibitory factor and fibroblast growth factor.

The invention also provides a process for preparing cells of a defined cell lineage comprising:
  (a) providing human embryonic stem (hES) cells;
  (b) growing the hES cells in vitro in a vessel under conditions under which the cells undergo differentiation and said cells or aggregates thereof do not adhere to the vessel wall;
  (c) incubating for a time sufficient to obtain at least one embryoid body (EB) containing cells of said defined cell lineage; and
  (d) isolating said cells from said EB.

In accordance with one embodiment, the cells of the defined cell lineage may be inoculated or transplanted into a human recipient to treat a certain human disease or condition, to allow tissue or organ repair, etc. Thus, in accordance with this preferred embodiment, the cells of the defined cell lineage are formulated in a manner to allow their inoculation or transplantation into the human recipient.

The present invention also provides, by another of its aspects, an inoculable or transplantable preparation comprising cells of said defined cell lineage together with a physiologically acceptable carrier which is compatible with said cells. The term "compatible with said cells" should be understood as a medium which ensures the viability of said cells until they are inoculated or transplanted into the human recipient.

The cells of the defined cell lineage may be induced to undergo further differentiation and transplanted or inoculated into the individual as a cell suspension or, alternatively, they may be cultivated to form a cell mass or an in vitro tissue, the mass or the tissue then being transplanted into the individual.

The hES cells from which the hEBs of the invention are derived may be obtained from established lines (e.g., see Thomson et al., 1998b, supra) or may be prepared de novo from human embryos which were produced by in vitro fertilization.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

MATERIALS AND METHODS

Formation of Human Cystic EBs

Human ES cells (H9 clone 10) were grown on mouse embryo fibroblasts in a culture medium consisting of 80% KnockOut™ DMEM (an optimized Dulbeco's modified Eagle's medium for ES cells, Gibco-BRL), 20% KnockOut™ SR (a serum-free formulation, Gibco-BRL), mM glutamine (Gibco-BRL), 0.1 mM β-mercaptoethanol (Sigma), 1% non-essential amino acids stock (Gibco-BRL), $10^3$ units/ml leukemia inhibitor factor (LIF) (Gibco-BRL) and 4 ng/ml basic fibroblast growth factor (bFGF) (Gibco-BRL). Under these conditions most of the cells are kept in an undifferentiated state. To induce formation of hEBs, the ES cells were transferred to plastic Petri dishes to prevent their adherence to the dish and promote their aggregation. The concentration of the cells was about $10^6$ cells per ml.

The hEBs were then cultured in the above culture medium not containing leukemia inhibitor factor or basic fibroblast growth factor.

Detection of Expression of Cell Specific Genes in Cystic hEBs.

Total RNA was extracted from cells as previously described (Chirgwin et al., 1979) and cDNA was synthesized from 1 μg of total RNA, using a random hexamer ($pd(N)_6$) as primer (Pharmacia Biotech) and M-LMV Reverse Transcriptase (Gibco-BRL). cDNA samples were subject to polymerase chain reaction (PCR) amplification with specific DNA primers. PCR was performed under linear conditions in order to reflect the original amount of the specific transcript. The PCR primers used and the reaction conditions were: α-fetoprotein: AGAACCTGTCA-CAAGCTGTG (SEQ ID NO:1) and GACAGCAAGCT-GAGGATGTC (SEQ ID NO:2)-Product: 676 base pairs (bp). 20 cycles at 60° C. in 1 mM $MgCl_2$; ζ-globin: GACTGAGAGGACCATCATTG (SEQ ID NO:3) and TCAGGACAGAGGATACGACC (SEQ ID NO:4)-Product: 397 bp. 25 cycles at 60° C. in 1 mM $MgCl_2$; GAPDH: AGCCACATCGCTCAGACACCA (SEQ ID NO:5) and GTACTCAGCGGCCAGCATCG (SEQ ID NO:6)-Product: 302 bp. 20 cycles at 60° C. in 1 mM $MgCl_2$. PCR products were analyzed by Western Blot hybridization (Southern, 1975). Probes were radiolabeled by random priming (Boehringer Mannheim) using $[\alpha-^{32}P]dCTP$ (3000 ci/mM, NEN-Life Science Products).

In Situ Hybridization Analysis of hEBs

EBs were stained with hematoxylin and eosin (H&E) or hybridized to specific RNA probes labeled with a fluorescent reagent (Grifman et al., 1998b) and 5 μm paraffin embedded serial sections were obtained. Control hybridizations were performed with non-specific RNA. The probes used were 50-mer 2'-O-methyl 5'-biotinylated cRNA of either α-fetoprotein-TTGTCCCTCTTCAGCAAAGCAGACTTCCT-GTTCCTGGCCTTGGCAGCATT (SEQ ID NO:7), ζ-globin-TGATGGTCCTCTCAGTCTTGGTCAGAGA-CATGGCGGCAGGGTGGGCAGCT (SEQ ID NO:8), Neurofilament 68 kd protein-CCTGCGTGCGGATGGACT-TGAGGTCGTTGCTGATGGCGGCTACCTGGCTC (SEQ ID NO:9), or α-cardiac actin-CGGTGGACAATG-GATGGGCCTGCCTCATCGTACTCTTGCTT-GCTAATCCA (SEQ ID NO:10).

EXAMPLES

Example 1

Formation of Cystic hEBs

Figure 1:
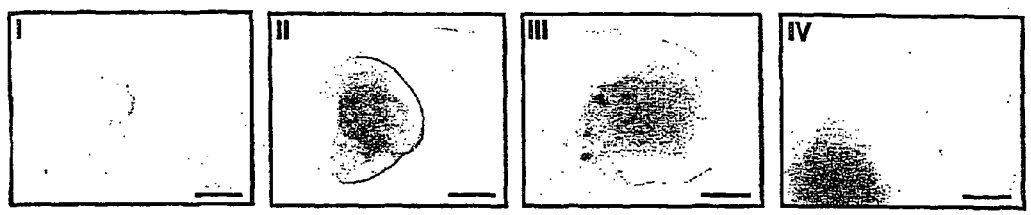
FIG. 1A shows cystic hEBs from 3 to 14 days after transfer to Petri dishes produced in accordance with the invention. I: simple EB; II & III: cavitated EB; IV: cystic hEB. Scale bar: 40 μm.
FIG. 1B shows 5 μm paraffin embedded sections of hEBs stained with hematoxylin and eosin (H&E, I-IV) or DAPI (V). I: scale bar 80 μm; II & III: scale bar 20 μm; IV: scale bar 4 μm.
Figure 1:
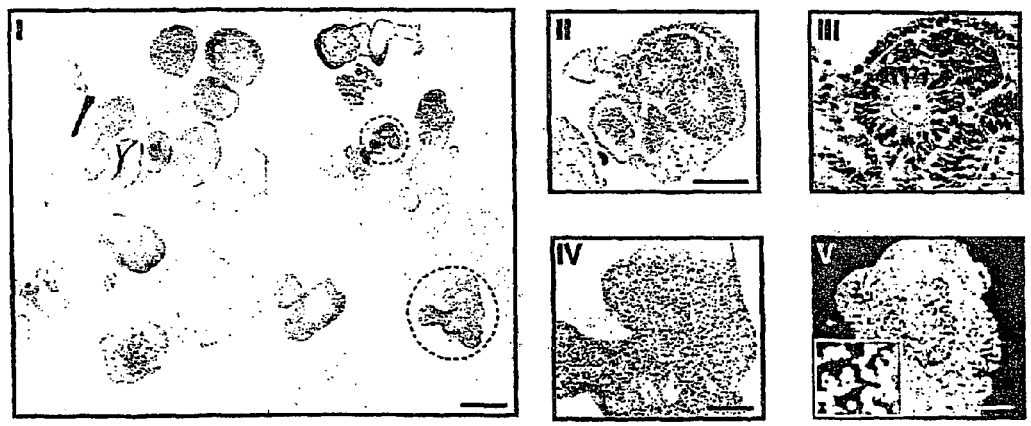

FIG. 1A shows several hEBs 3 to 14 days after having been transferred to plastic Petri dishes and cultured in medium not containing leukemia inhibitor factor or basic fibroblast growth factor. Initially, simple hEBs form (FIG. 1A-I). Subsequently, the center of the bodies became cavitated (FIG. 1A. II and III), and the bodies began to accumulate fluid, turning to cystic hEBs (FIG. 1A, IV). 20 days after initiation of cellular aggregation most of the structures were cystic and they included a variety of epithelial and mesenchymal cells. FIG. 1B shows 5 μm paraffin embedded sections of 20 day old hEBs stained with H&E (I-IV) or DAPI (V). DAPI staining of the nuclei revealed in some of the cells condensed chromatin that probably corresponds to the apoptosis occurring in the center of the hEB (FIG. 1B-III).

Example 2

Expression of Cell Specific Genes in Cystic hEBs

Figure 2:
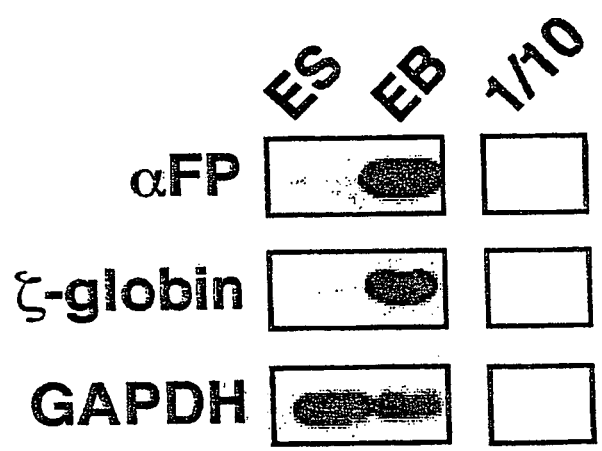
FIG. 2 shows the expression of cell specific genes in hES cells and cystic hEBs.

In order to examine the differentiation status of the EBs, RNA was extracted from hES cells grown on mouse embryo fibroblasts, and from 20 day old EBs. cDNA was synthesized using these RNA samples and expression analysis of several genes was performed by RT-PCR with various human specific DNA primers. The RT-PCR analysis was performed under non-saturating linear conditions. The identity of the amplified DNA product in the PCR assay was verified by sequence analysis. The lane marked EB in FIG. 2 shows that the hEBs express α-fetoprotein (αFP), an endodermal marker (Krumlauf et al., 1985), and ζ-globin, a marker of hematopoietic cells (Leder et al., 1985). Very low levels of these markers were observed in the hES cells (Lane ES). The housekeeping gene glyceraldehyde-3-phosphate dehydrogenase (GAPDH) served as an internal control. Linearity of the observed signal is demonstrated by the "1/10 column" showing a PCR assay performed with one-tenth the amount of cDNA used in the PCR assay of the hEB sample.

Example 3

In Situ Hybridization Analysis of hEBs

Figure 3:
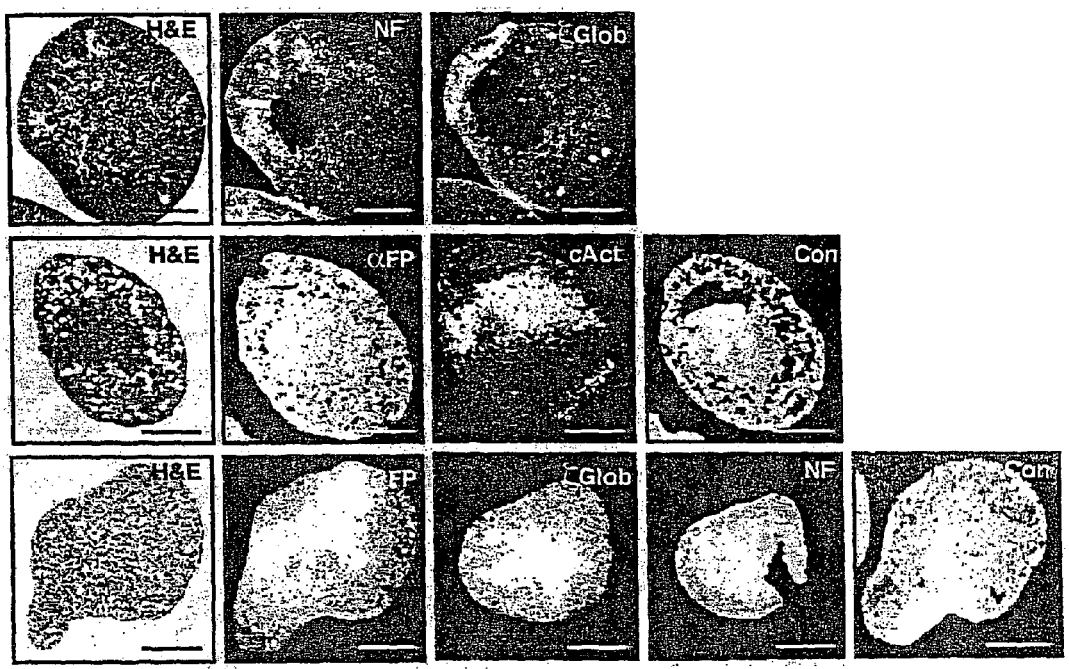
FIG. 3 shows in situ hybridization analysis of expression of α-fetoprotein (αFP), ζ-globin (ζ-Glob), neurofilament 68 ltd protein (NF) and α-cardiac actin (cAct) in 20 day old EBs (Con indicates control)

To regionally characterize the differentiating cells within the EBs by in situ hybridization, expression of four cell-specific molecular markers, all of which transcribe very early during embryonic differentiation, was examined. Serial sections of the hEBs were hybridized with RNA probes specific to α-fetoprotein (αFP) (Krumlauf et al., 1985), ζ-globin (ζ-glob) (Leder I., 1985), α-cardiac actin (cAct) (Sassoon et al., 1988) or neurofilament 68 kd protein (NF) (Julien et al., 1986). As shown in FIG. 3, each of these molecular probes specifically labels distinct regions in the EBs. This suggests that the labeled cells in each section were either clonal (derived from a common progenitor cell), or were affected by the same signals and differentiated into the same specific lineage.

Example 4

Characterization of a Pulsating hEB

Figure 4:
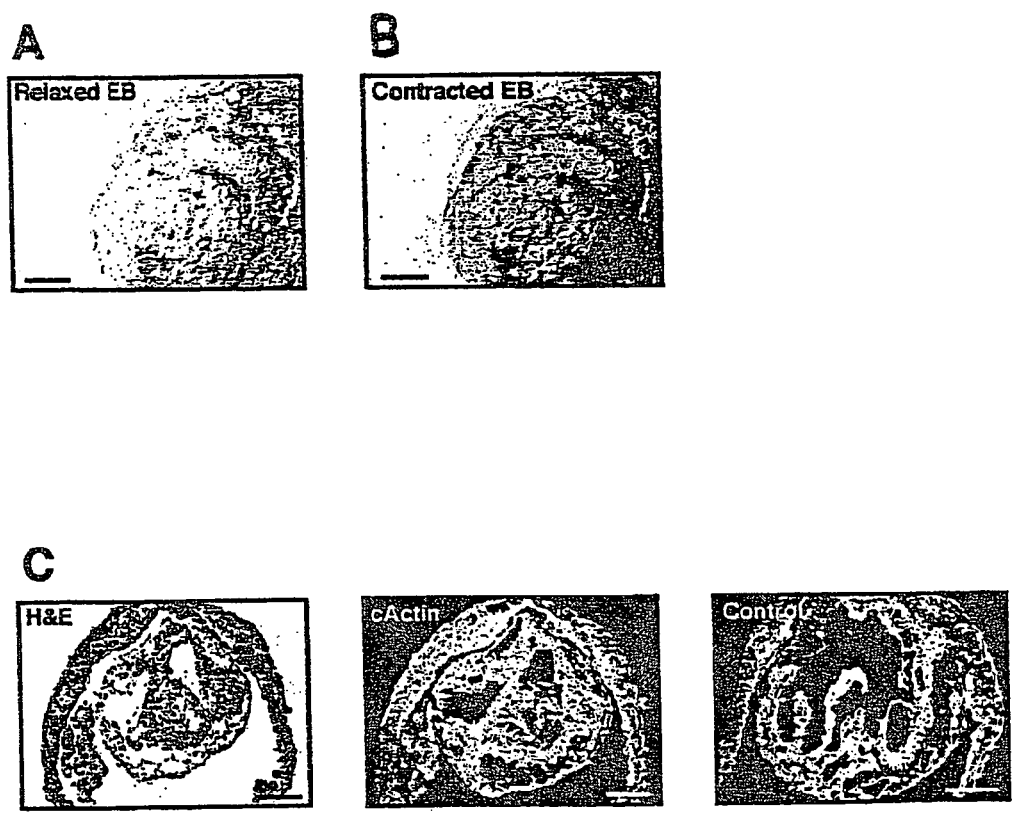
FIG. 4A shows a pulsating hEB in a relaxed state. Scale bar, 40 μm.
FIG. 4B shows the pulsating hEB of FIG. 4A in a subsequent contracted state. Scale bar, 40 μm.
FIG. 4C shows serial sections from a pulsating hEB including a section stained with H&E, a hybridized section showing α-cardiac actin expression (cActin), and a control section hybridized with non-specific RNA (Control). Scale bar, 100 μm.

Differentiation of murine ES cells in EBs into the myocardial lineage has been shown to produce pulsating muscle (Sanchez et al., 1991). The existence of cardiac muscle cells in hEBs was demonstrated by in situ hybridization of sections from a human EB with α-cardiac actin, a marker of embryonic myocardial cells (Sassoon et al., 1988). FIGS. 4A and B show a large vacuated hEB including cardiac muscle cells that were pulsating at a rate of about 30 beats/min. The hEB was first photographed in a relaxed state (FIG. 4A) and then subsequently in a contracted state (FIG. 4B). FIG. 4C shows serial sections of a cell including a section stained with hematoxylin and eosin (H&E), a hybridized section showing α-cardiac actin expression (cActin), and a section hybridized with non-specific RNA (Control).

REFERENCES

Bain, G., Kitchens, D., Yao, M., Huettner, J. E., Gottlieb, D. I., *Developmental Biology*, 168:342-57 (1995).
Capecchi, M. R., *Science*, 244: 1288-92 (1989).
Chirgwin, J. M., Przybyla, A. E., Macdonald, R. J., Rutter, W. J., *Biochemistry*, 18:5294-9 (1979).
Dushnik-Levinson, M., Benvenisty, N., *Biology of the Neonate*, 67:77-83, (1995).
Julien, J. P., Meyer, D., Flavell, D., Hurst, J., Grosveld, *Brain Research*, 387:243-50 (1986).
Krumlauf, R., Hammer, R. E., Tilghman, S. M., Brinster, R. L., *Molecular and Cellular Biology*, 5: 1639-48 (1985).
Leder, A., Weir, L., Leder, P., *Molecular and Cellular Biology*, 5:1025-33 (1985).
Levinson-Dushnik, M., Benvenisty, N., *Molecular and Cellular Biology*, 17:3817-22 (1997).
Lindenbaum, M. H., Grosveld, F, *Genes and Development*, 4:2075-85 (1990).
Robertson, E., in *Teratocarcinoma and Embryonic Stem Cells: A Practical Approach*, R. EJ, Eds. (IRL Press, Oxford, 1987) pp. 71-112.
Rossant, A. L. Joyner, *Trends in Genetics*, 5:277-83 (1989).
Sanchez, A., Jones, W. K., Gulick, J., Doetschman, T., Robbins, J., *Journal of Biological Chemistry*, 266:22419-26 (1991).
Sassoon, D. A., Garner, I., Buckingham, M., *Development*, 104:155-(1988).
Southern, E. M., *Journal of Molecular Biology*, 98:503-17 (1975).
Thomson, J. A., et al., *Biology of Reproduction*, 55:254-9 (1996).
Thomson, J. A., et al., *Proceedings of the National Academy of Sciences of The United States of America*, 92:7844-8 (1995).
Thomson, J. A. and Marshall, V. S., *Curr. Top. Dev. Biol.* 38, 133 (1988a)
Thomson, J. A., et al., *Science*, 282:1145-7 (1998b).
Wiles, M. V., Keller, G., *Development*, 111:259-67 (1991).
Wobus, A. M., Holzhausen, H., Jakel, P., Schoneich, J., *Experimental Cell Research*, 152:212-9(1984).

The invention claimed is:

1. A process for obtaining at least one human-derived embryoid body (hEB), comprising:
   (a) providing human embryonic stem (hES) cells;
   (b) growing the hES cells in vitro suspended in a liquid growth medium in a vessel under conditions under which said cells undergo differentiation and said cells or aggregates thereof do not adhere to the vessel wall, wherein said conditions comprise culturing cells in a vessel having walls of a kind to which cells do not adhere; and
   (c) incubating for a time sufficient to develop hEBs from said cells.

* * * * *